(12) United States Patent
Wilder et al.

(10) Patent No.: US 11,779,194 B2
(45) Date of Patent: Oct. 10, 2023

(54) LOCKING MECHANISMS FOR ENDOSCOPIC DEVICES

(71) Applicant: Boston Scientific Scimed, Inc., Maple Grove, MN (US)

(72) Inventors: Evan Wilder, Boston, MA (US); Scott E. Brechbiel, Acton, MA (US); James Weldon, Newton, MA (US); Bridget Stanford, Reading, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 122 days.

(21) Appl. No.: 17/223,295

(22) Filed: Apr. 6, 2021

(65) Prior Publication Data
US 2021/0315445 A1 Oct. 14, 2021

Related U.S. Application Data

(60) Provisional application No. 63/006,784, filed on Apr. 8, 2020.

(51) Int. Cl.
*A61B 1/00* (2006.01)
*A61B 1/005* (2006.01)
*A61B 1/018* (2006.01)

(52) U.S. Cl.
CPC ...... *A61B 1/00066* (2013.01); *A61B 1/00042* (2022.02); *A61B 1/0052* (2013.01);
(Continued)

(58) Field of Classification Search
CPC ... A61B 1/018; A61B 1/00098; A61B 1/0052; A61B 1/0058
See application file for complete search history.

(56) References Cited

U.S. PATENT DOCUMENTS

| | | | |
|---|---|---|---|
| 2002/0091303 A1* | 7/2002 | Ootawara | A61B 1/01 600/106 |
| 2003/0073955 A1* | 4/2003 | Otawara | A61B 1/00098 600/101 |

(Continued)

FOREIGN PATENT DOCUMENTS

| | | |
|---|---|---|
| DE | 10 2012 012877 | 1/2014 |
| EP | 2 710 949 | 3/2014 |
| WO | WO 2017/011535 | 1/2017 |

OTHER PUBLICATIONS

International Search Report and Written Opinion issued in International Application No. PCT/US2021/025900, dated Jul. 23, 2021 (13 pages).

*Primary Examiner* — Anh Tuan T Nguyen
*Assistant Examiner* — Rynae E Boler
(74) *Attorney, Agent, or Firm* — Bookoff McAndrews, PLLC

(57) ABSTRACT

A medical device may comprise a sheath configured to be inserted into a body lumen of a patient. A distal end of the sheath may include an elevator for changing an orientation of a medical device. A handle may include an actuator. The actuator may be operably connected to the elevator. Activation of the actuator may cause movement of the elevator. An engaging portion may, in at least one configuration of the handle, protrude from a surface of a handle body toward the actuator. A force exerted by the user on at least one of the actuator or the engaging portion may cause the handle to transition between (a) a first configuration in which the engaging portion interacts with the actuator to inhibit movement of the actuator relative to the engaging portion and (b) a second configuration in which the actuator is movable relative to the engaging portion.

11 Claims, 11 Drawing Sheets

(52) U.S. Cl.
CPC ........ *A61B 1/0058* (2013.01); *A61B 1/00098* (2013.01); *A61B 1/018* (2013.01)

(56) References Cited

U.S. PATENT DOCUMENTS

| | | | |
|---|---|---|---|
| 2007/0232857 A1* | 10/2007 | Otawara | A61B 1/00177 600/129 |
| 2014/0260724 A1* | 9/2014 | Currier | F16H 19/0672 74/89.2 |
| 2016/0089003 A1* | 3/2016 | Morimoto | A61B 1/00066 600/107 |
| 2016/0089004 A1* | 3/2016 | Morimoto | A61B 1/00179 600/107 |
| 2016/0089124 A1* | 3/2016 | Morimoto | A61B 1/00098 606/205 |
| 2016/0089125 A1* | 3/2016 | Morimoto | A61B 1/00098 600/107 |
| 2017/0020548 A1* | 1/2017 | Levasseur | A61B 1/00135 |
| 2019/0247083 A1 | 8/2019 | Worrell et al. | |
| 2021/0236204 A1* | 8/2021 | Tower | A61B 1/00066 |

\* cited by examiner

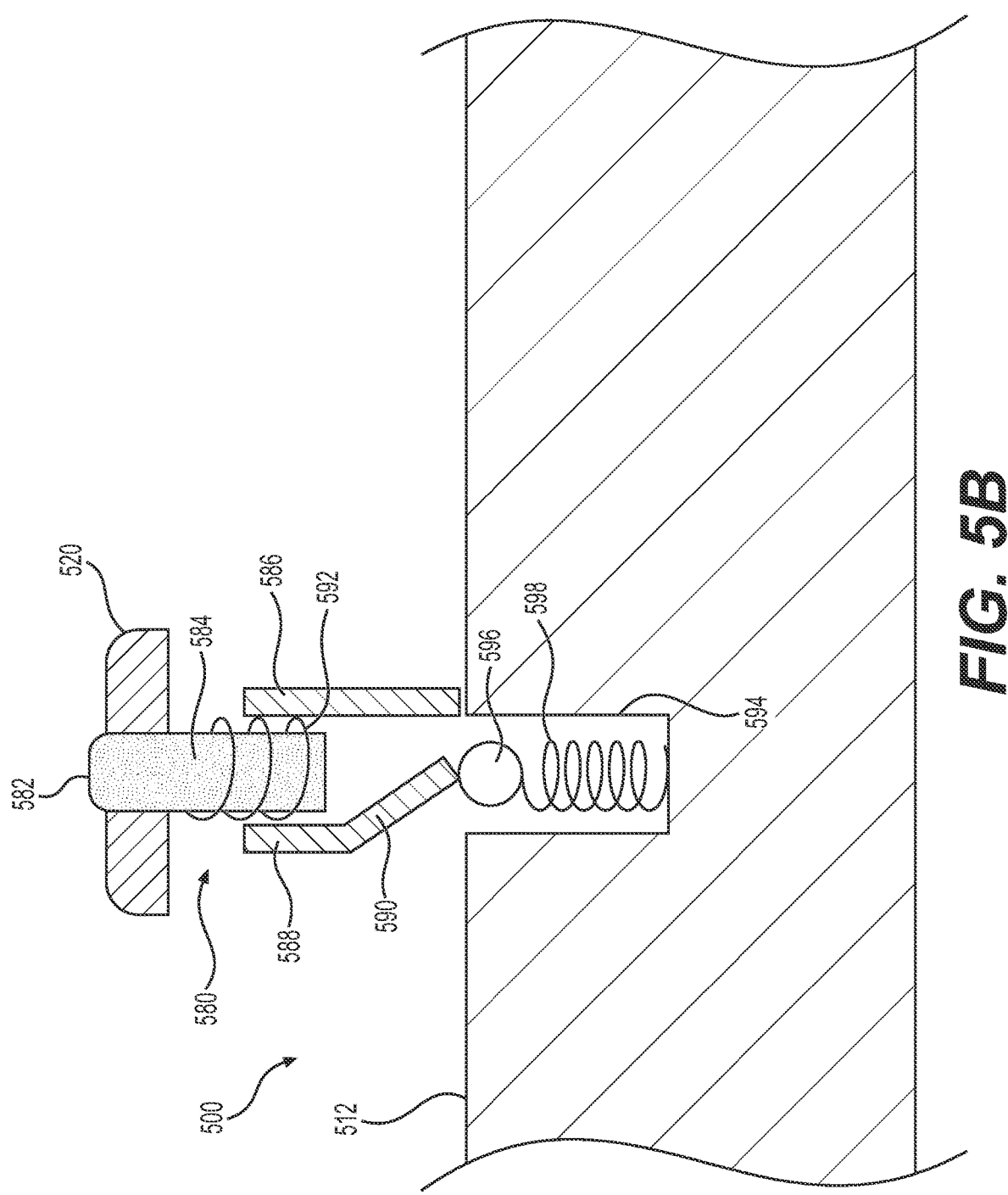

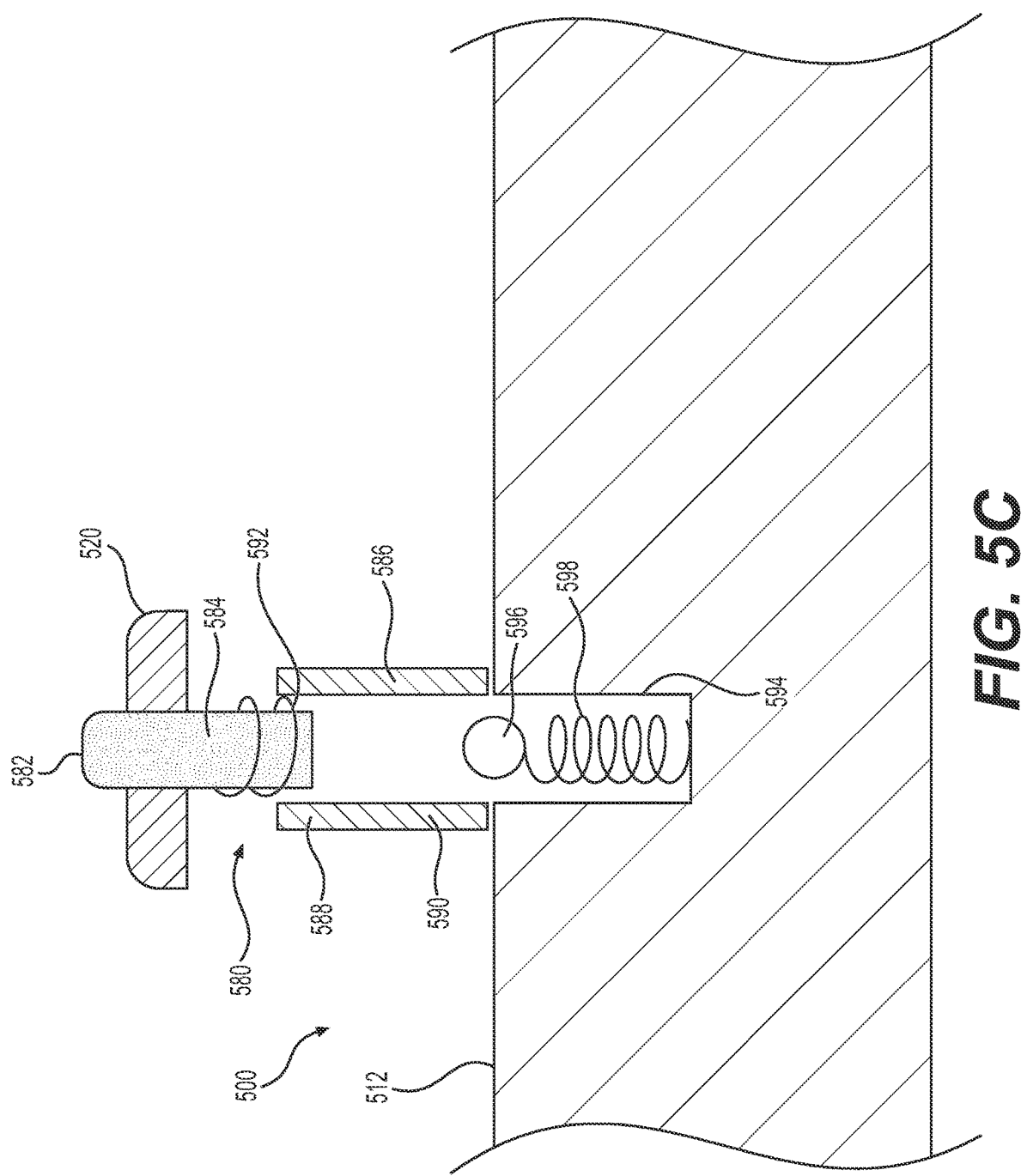

LOCKING MECHANISMS FOR ENDOSCOPIC DEVICES

CROSS-REFERENCE TO RELATED APPLICATIONS

This application claims the benefit of priority from U.S. Provisional Application No. 63/006,784, filed on Apr. 8, 2020, which is incorporated by reference herein in its entirety.

TECHNICAL FIELD

Various aspects of this disclosure relate generally to devices and methods for inhibiting movement of components of medical devices. In embodiments, the disclosure relates to devices for locking components of handles of duodenoscopes.

BACKGROUND

Duodenoscopes may include a handle portion, which may be gripped by an operator and may include control elements for functions such as steering, suction, water, air, light, and imaging. A duodenoscope may also include a portion which may be inserted into a subject. For example, a duodenoscope may include a shaft suitable for insertion into a subject. Such an insertion portion may include one or more lumens. The lumens of an insertable portion of a duodenoscope may support functions, for example, conveying air, water, suction, electricity, data, light, and/or images. Tools may also be inserted via a working channel of the shaft. For example, a tool may be inserted by a port in or near the handle of a duodenoscope into the working channel.

A distal tip of a duodenoscope may include an elevator for changing an orientation of a tool projecting from a distal end of a working channel. An elevator may be controlled via a control mechanism in a handle, such as a lever.

SUMMARY

Each of the aspects disclosed herein may include one or more of the features described in connection with any of the other disclosed aspects.

A medical device may comprise a sheath configured to be inserted into a body lumen of a patient. A distal end of the sheath may include an elevator for changing an orientation of a medical device. A handle may have a handle body. The handle may include an actuator. The actuator may be operably connected to the elevator. Activation of the actuator may cause movement of the elevator. The actuator may be configured to be contacted by a user. An engaging portion may, in at least one configuration of the handle, protrude from a surface of the handle body toward the actuator. A force exerted by the user on at least one of the actuator or the engaging portion may cause the handle to transition between (a) a first configuration in which the engaging portion interacts with the actuator to inhibit movement of the actuator relative to the engaging portion and (b) a second configuration in which the actuator is movable relative to the engaging portion.

Any of the medical devices disclosed herein may include any of the following features. The actuator may include a lever. The actuator may include a protrusion extending radially inward toward a surface of the handle body. The protrusion may have a wedge shape. The engaging portion may include a hook. In the first configuration, the protrusion may engage with the hook. The hook may be movable to cause the handle to transition from the first configuration to the second transition. The hook may include a first portion that protrudes radially outward from the handle body in at least the first configuration of the handle, and a second portion that protrudes radially outward from the handle body in at least the first configuration of the handle. The first portion may be configured to engage with the protrusion in the first configuration of the handle. The second portion may be configured to be pressed radially inward by a user in order to transition the handle from the first configuration to the second configuration. The engaging portion may include a shape memory material. The handle may further include a button configured to exert a force on the second portion. The handle may be configured to be transitioned from the second configuration to the first configuration by moving the protrusion from a first side of the first portion to a second side of the first portion. The second side may be opposite the first side. The engaging portion may include a plurality of teeth. The handle may be transitioned from the first configuration to the second configuration by moving a first portion of the actuator relative to a second portion of the actuator. The engaging portion may exert a frictional force on the actuator to inhibit movement of the actuator in the first configuration. The engaging portion may include a body and a spring disposed in a cavity of the handle body. The actuator may include a wall. In the first configuration, a first portion of the wall may have a first angle with respect to a surface of the handle body. In the second configuration, the first portion of the wall may have a second with respect to the surface of the handle body. The second angle may be different from the first angle. The actuator may be movable in a first direction and a second direction in order to cause movement of the elevator. In order to transition the handle from the first configuration to the second configuration, the actuator may be moved in a third direction, approximately perpendicular to each of the first direction and the second direction.

In another example, a medical device may comprise a sheath configured to be inserted into a body lumen of a patient. A distal end of the sheath includes an elevator for changing an orientation of a medical device. A handle may have a handle body. The handle may include an actuator. The actuator may be operably connected to the elevator. Activation of the actuator may cause movement of the elevator. The actuator may be configured to be contacted by a user. An engaging portion, in at least one configuration of the handle, may protrude from a surface of the handle body toward the actuator. An interaction between the engaging portion and the actuator may be configured to lock the actuator, thereby inhibiting movement of the elevator. Pressing a button on at least one of (a) a surface of the handle body or (b) the actuator may be configured to unlock the actuator, thereby allowing movement of the elevator.

Any of the medical devices described herein may have any of the following features. The actuator may include a lever. The actuator may include a protrusion extending radially inward toward a surface of the handle body. The engaging portion may include a hook. The protrusion may engage with the hook to lock the elevator. The button may cause the hook to move in order to unlock the elevator.

In an example, a method may comprise contacting an actuator and exerting a force on the actuator in order to move the actuator from a first position to a second position, thereby (a) raising an elevator of a distal tip of a duodenoscope from a lowered configuration to a raised configuration and (b) causing the actuator to encounter an engaging portion on a surface of a handle body of the duodenoscope and ceasing contact with the actuator. After contact with the actuator is ceased, the elevator may be retained in the raised configuration. A force may be exerted on the actuator or the engaging portion. The elevator may be moved from the second position to the first position, thereby lowering the elevator from the raised configuration to the lowered configuration.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "diameter" may refer to a width where an element is not circular. The term "distal" refers to a direction away from an operator, and the term "proximal" refers to a direction toward an operator. The term "exemplary" is used in the sense of "example," rather than "ideal." The term "approximately," or like terms (e.g., "substantially"), includes values +/−10% of a stated value.

BRIEF DESCRIPTION OF THE DRAWINGS

The accompanying drawings, which are incorporated in and constitute a part of this specification, illustrate aspects of the present disclosure and together with the description, serve to explain the principles of the disclosure.

DETAILED DESCRIPTION

After activating an elevator, it may be desirable for an operator to be able to retain the elevator in a desired position without maintaining contact on a control mechanism used to activate the lever. Therefore, a need exists for locking mechanisms for duodenoscope components such as elevators. Embodiments of this disclosure relate to locking mechanisms of inhibiting motion of an elevator control lever when the lever is in one or more predetermined positions. The locking mechanisms may, for example, lock the elevator lever so that the elevator is retained in a raised position. After the elevator is locked, a user may be able to remove a finger or thumb from the elevator lever, freeing the user to conduct other operations with that finger or thumb.

Figure 1A:
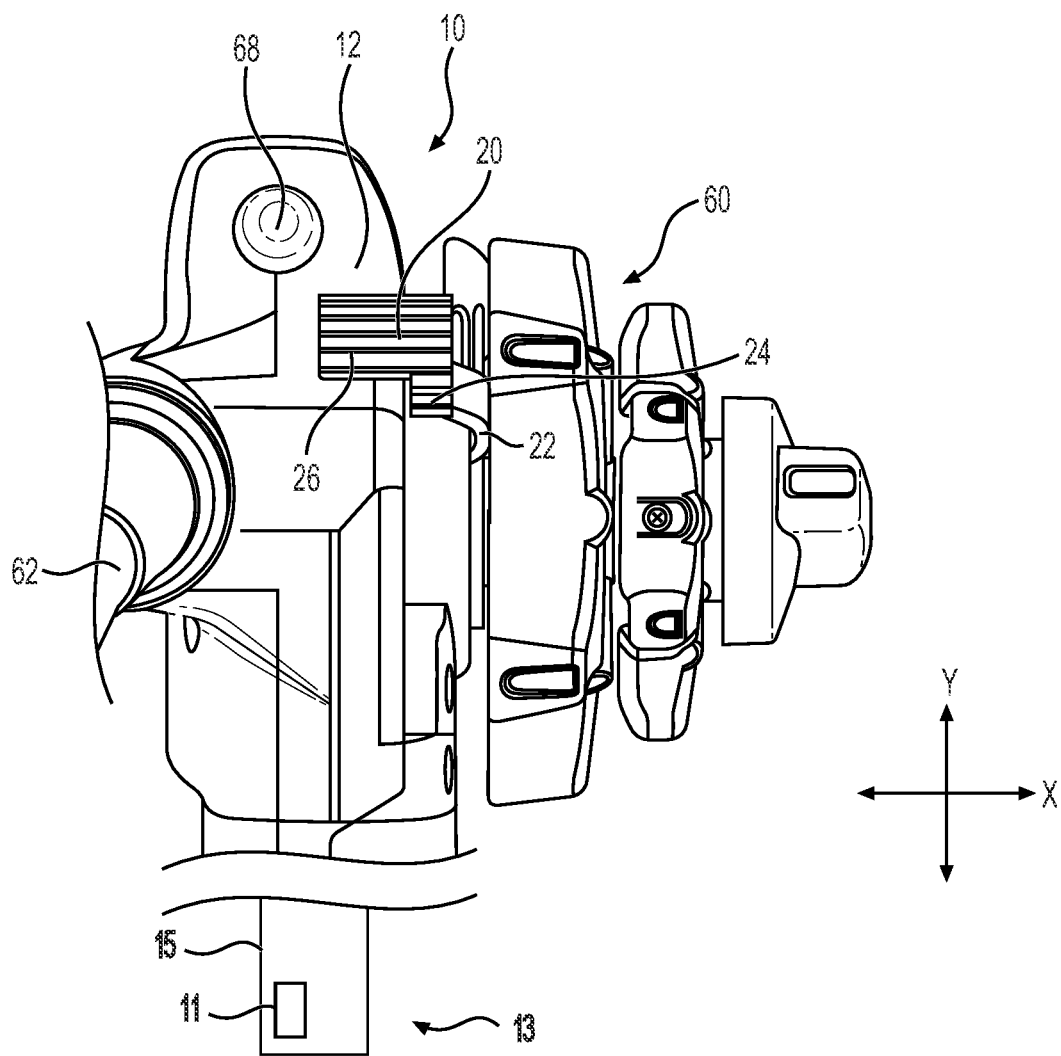
FIGS. 1A and 1B show aspects of an exemplary handle.
Figure 1B:
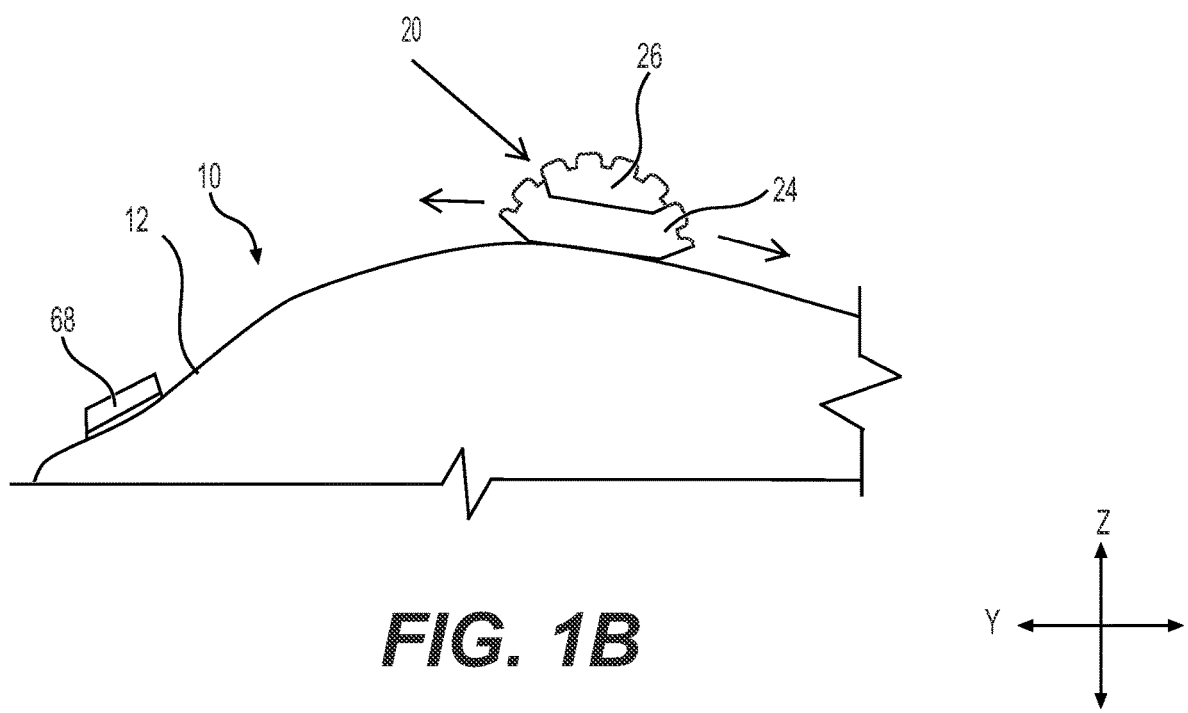

FIGS. 1A and 1B show different views of a duodenoscope handle 10. Although the term duodenoscope may be used herein, it will be appreciated that other devices, including, but not limited to, endoscopes, colonoscopes, ureteroscopes, bronchoscopes, laparoscopes, sheaths, catheters, or any other suitable delivery device or medical device may be used in connection with the disclosed locking mechanisms. Relative to the view in FIG. 1A, the view in FIG. 1B has been rotated relative to the view in FIG. 1A, as shown by the coordinate systems on FIGS. 1A and 1B. As shown in FIG. 1A, handle 10 may include a body 12. An elevator actuator, such as a lever 20 may be moved in the directions shown by the arrow in FIG. 1B to provide control over an elevator 11 at a distal end 13 of an endoscope (shown in FIG. 1A). Although a lever 20 is depicted, alternative control mechanisms may fall under the scope of this disclosure. For example, sliders, knobs, switches, wheels, or other mechanisms may be used. Lever 20 may include an arm 24 and a contact portion 26, which may extend radially outward from arm 24 (to the left in FIG. 1A and out of the page in FIG. 1B). Arm 24 may extend into handle 10, connecting to a wire or other structure (e.g., a shaft) that extends through a shaft 15 of the endoscope (shown in FIG. 1A) and connects to elevator 11 at the distal end 13 of the endoscope. Movement of arm 24 may cause elevator 11 to raise or lower.

Contact portion 26 may extend approximately parallel to a surface of body 12. Contact portion 26 may extend approximately perpendicularly to arm 24. Contact portion 26 may include ridges or other features to increase friction and or facilitate gripping between contact portion 26 and a user's finger or thumb.

Handle 10 may also include a steering assembly 60, which may include knobs and/or levers for articulating distal end 13 of the endoscope. An umbilicus 62 may extend from handle 10 and may house cables, cords, wires, and/or conduits for providing signals, power, air, and/or water to handle 10 and other portions of the endoscope. An image capture button 68 may allow for control of a camera on distal end 13 of the endoscope in order to capture still images. Handle 10 may also have other features, such as ports and valves (e.g., for air, water, and/or suction).

FIGS. 2A-6B depict various locking mechanisms. The locking mechanisms of FIGS. 2A-6B may be used along with handle 10 or with alternative handles. Aspects of the locking mechanisms described herein may be used alone or in combination. Where practical, like reference numbers have been used herein to denote similar structures. Unless stated otherwise, handles described below may have any of the features of handle 10. Although the figures depict locking mechanisms for locking a lever and an elevator, such as, for example, elevator 11 shown in FIG. 1A, in one position, it will be appreciated that a plurality of locking mechanisms may be used for locking the lever and the elevator at various positions. Although the locking mechanisms are described relative to an elevator lever and an elevator, it will be appreciated that the locking mechanisms may alternatively be used with other components (e.g., steering components). Although the locking mechanisms are described relative to an elevator lever and an elevator, it will be appreciated that the locking mechanisms may alternatively be used with other components (e.g., steering components).

Figure 2A:
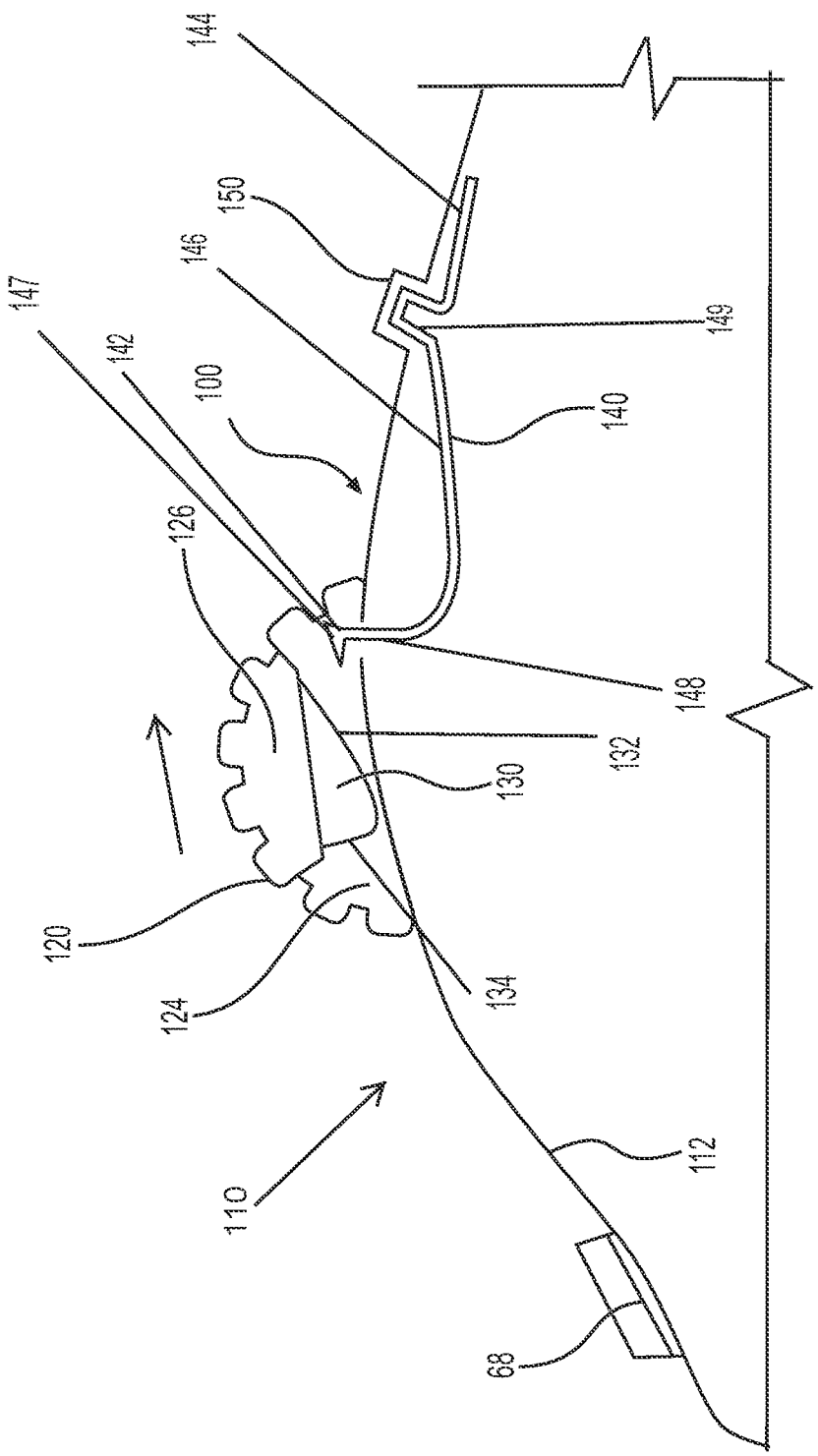
FIGS. 2A-6B show exemplary locking mechanisms.
Figure 2B:
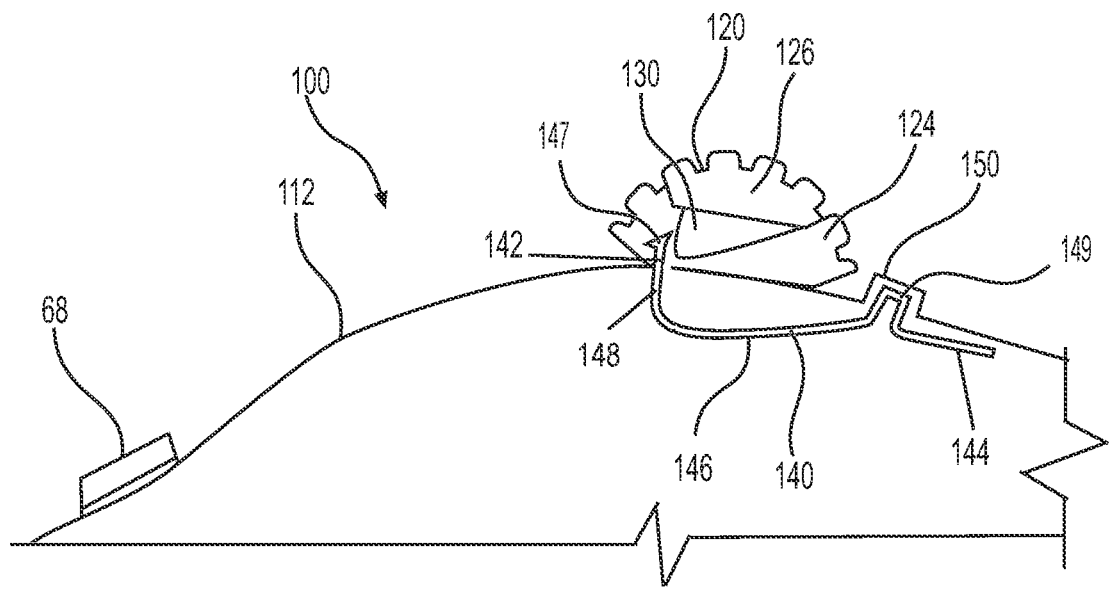
Figure 2C:
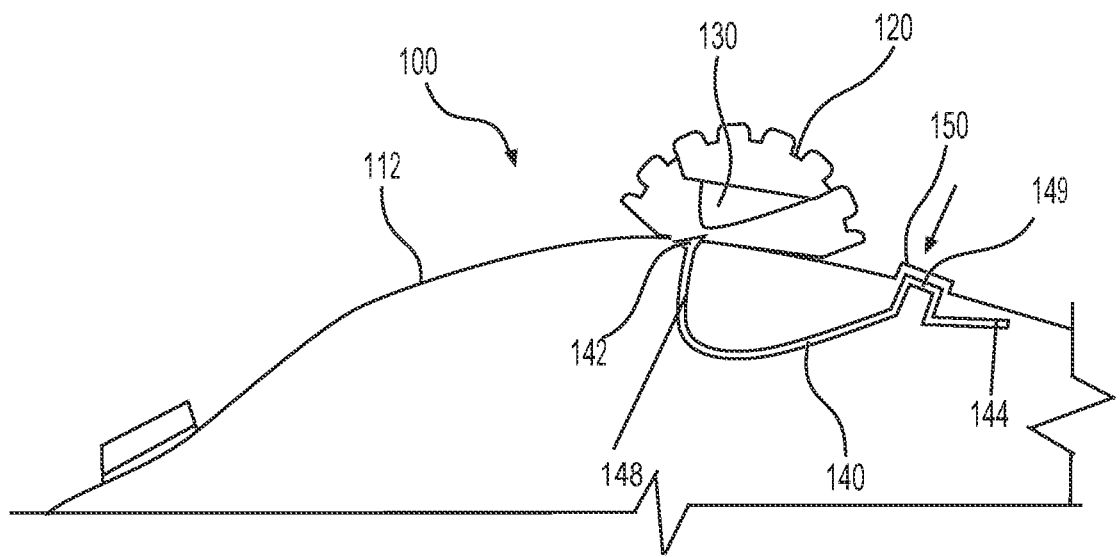

FIGS. 2A-2C show a first exemplary locking mechanism 100. Locking mechanism 100 may include an actuator, such as a lever 120 having an arm 124 and a contact portion 126. Lever 120, arm 124, and contact portion 126 may have any of the features of lever 20, arm 24, and contact portion 26, respectively. Handle 110, including body 112, may have any of the properties of handle 10 and body 12, respectively. For example, an image capture button 68 may be disposed on a surface of body 112. Body 112 is shown as being transparent in FIGS. 2A-2C in order to show a hook 140 (which may be an engaging portion), described below. It will be appreciated that other components, aside from hook 140, within body 112 are not shown, for clarity of illustration.

FIG. 2A shows locking mechanism 100 in a first, unlocked configuration. Lever 120 is freely movable (subject to other constraints, such as a stop at the end of a range of lever 120). The arrow in FIG. 2A shows the direction in which lever 120 is moving in order to transition locking mechanism 100 into the second, locked configuration of FIG. 2B. In FIG. 2B, lever 120 is not movable in a first direction (generally to the left in FIGS. 2A-2C). Lever 120 may also not be movable in a second direction (generally to the right in FIGS. 2A-2C) because a stop or other feature on arm 124, another portion of lever 120, and/or within body 112 of handle 110 inhibits movement of lever 120 in the second direction past the position shown in FIG. 2B.

Lever 120 may also include a protrusion or catch 130 extending from a surface of contact portion 126 facing a surface of body 112. Protrusion 130 may extend radially inward toward a surface of body 112 from contact portion 126. Protrusion 130 may have any suitable shape. As shown in FIGS. 2A-2C, protrusion 130 may have a triangular or wedge shape. A first side 132 of protrusion 130 may be slanted or tapered radially outward toward a surface of body 112 moving in the first direction (to the left in FIGS. 2A-2C). First side 132 may be straight or may be slightly curved, as shown in FIGS. 2A-2C. A second side 134 of protrusion 130 may extend between an end of first side 132 that is furthest in the first direction and a radially inward surface of contact portion 126.

A majority of hook 140 may be disposed within body 112, though a portion of hook 140 may extend outside of body 112 as will be explained. Hook 140 may extend from a first end 142 (furthest in the first direction) to a second end 144 inside of body 112 (furthest in the second direction). A shaft 146 may extend from first end 142 toward second end 144. A hooked portion 148 may extend transversely from shaft 146. For example, hooked portion 148 may extend at an angle of approximately 90 degrees from shaft 146. First end 142 may terminate in a barb 147 and may be shaped similarly to an end of a fishhook. In at least some configurations, as described below, first end 142 (and barb 147) may extend radially outward through an opening of body 112 so that first end 142 extends externally of body 112.

A protruding portion 149 of shaft 146 may be bent to form an approximately "U" shape. Protruding portion 149 may extend radially outward from a longitudinal axis of hook 140. Except for protruding portion 149, shaft 146 may be approximately straight or may be slightly curved.

Protruding portion 149 may be aligned with and may extend into a button 150 on a surface of body 112. Button 150 may have any suitable components. For example, button 150 may be formed of flexible material or rigid material. Button 150 may include resilient and/or shape memory components so that button 150 is biased into the undepressed configuration of FIGS. 2A-2B. For example, button 150 may include a spring, or a portion of button 150 contactable by a user may include shape-memory material. Button 150 may have interior surfaces configured to mate with protruding portion 149 and retain protruding portion 149 via friction fit. Additionally or alternatively, adhesive or other mechanisms may be used to retain protruding portion 149 within button 150.

Lever 120 may be transitioned among the different configurations of FIGS. 2A-2C. In the configuration of FIG. 2A, lever 120 may be in a position such that the elevator is in a lowered position or a partially raised position, and lever 120 may be movable in the first and/or second directions (approximately to the left or the right in the figures, respectively) in order to raise or lower the elevator. In the configuration of FIG. 2B, lever 120 may be in a position such that the elevator is in a raised position, and lever 120 may be locked and therefore inhibited from moving in the first direction. The elevator may accordingly be inhibited from moving into a lowered position. Alternatively, the locked position of lever 120 in FIG. 2B may correspond to other configurations of the elevator (e.g., lowered or partially raised).

In the first configuration shown in FIG. 2A, button 150 may be in a relaxed configuration, and lever 120 may be positioned further in the first direction than first end 142 of hook 140, including barb 147. In particular, second side 134 of protrusion 130 may be further in the first direction than first end 142 of hook 140. In the first configuration of FIG. 2A, lever 120 may be freely movable because it is not engaged with hook 140. Lever 120 may be in an unlocked configuration.

Hook 140 may be positioned within body 112 such that second end 144 is positioned proximate to or touching an inner surface of body 112. Second end 144 may have approximately the same position in each of the configurations of FIGS. 2A-2C. Protrusion 149 may extend radially outward of a surface of body 112, into relaxed button 150. A user may be able to contact button 150 and thereby transmit a radially inward force on protrusion 149.

To transition lever 120 and hook 140 from the first configuration of FIG. 2A to the second configuration of FIG. 2B, lever 120 may be moved in the second direction (approximately to the right in FIGS. 2A-2C). First side 132 of protrusion 130 may slide over first end 142 of hook 140, including barb 147. Shapes of first side 132 and first end 142 of hook 140, including barb 147, may be complementary so that first side 132 of protrusion 130 may slide past first end 142 of hook 140. Contact between first side 132 of protrusion 130 and first end 142 of hook 140 may provide tactile feedback to a user and indicate a position of lever 120 and/or an elevator controlled by lever 120.

As first side 132 of protrusion 130 moves in the second direction past first end 142 of hook 140, first side 132 may exert a radially inward force on first end 142, so that first end 142 is pushed radially inward. An angle of a radially outward side of barb 147 and first side 132 of protrusion 130 may be approximately parallel or otherwise complementary in order to facilitate protrusion 130 in sliding past barb 147. Second end 144 may remain approximately stationary. As hook 140 is pushed radially inward, hook 140 may adopt a configuration similar to that shown in FIG. 2C, discussed in further detail below. However, as compared to the configuration of FIG. 2C, button 150 may remain undepressed as protrusion 130 moves past first end 142 to transition from the first configuration of FIG. 2A to the second configuration of FIG. 2B.

Hook 140 may be biased such that, after an entirety of protrusion 130 moves past first end 142 (so that, as shown in FIG. 2B, protrusion 130 is on an opposite side of first end 142 as in the first configuration of FIG. 2A), first end 142 may return to its original position, in which first end 142 (including barb 147) extends radially outward of a surface of body 112, toward protrusion 130. Hook 140, after returning to its biased position, may have the same shape as in the first configuration of FIG. 2A.

In the configuration of FIG. 2B, first end 142 of hook 140, including barb 147, may extend radially outward past a radially inwardmost end of second side 134 of protrusion 130. First end 142 of hook 140 may inhibit movement of protrusion 130 and, accordingly, lever 120, in the first direction (to the left in the Figures). Forces (from a user or other types of forces) on lever 120 in the first direction may cause second side 134 of protrusion 130 to contact hooked portion 148 of hook 140, including first end 142 and/or barb 147. A force exerted by hook 140 on protrusion 130 may be in approximately the second direction and may inhibit movement in the first direction. For example, as shown in FIGS. 2A-2C, hooked portion 148 and second side 134 may be approximately parallel to one another.

In order to unlock lever 120 (and therefore allow movement of the elevator controlled by lever 120), button 150 may be depressed by a user, as shown in the third configuration of FIG. 2C. Button 150 may exert a radially inward force on protruding portion 149, which may, in turn, cause at least portions of hook 140 to move radially inward. Alternatively, button 150 may be omitted and a user may press directly on protruding portion 149 or another portion of hook 140. Hook 140 may be connected to a spring or possess shape memory properties so that hook 140 is biased in the shape of FIGS. 2B-2C. For example, hook 140 may be made of nitinol or another material (e.g., metal or plastic). As a further alternative, other suitable mechanisms may be used to press portions of hook 140 (including second end 144) radially inward. Hook 140 may have any suitable shape for accomplishing the transition of first end 142 between the position of FIGS. 2A, 2B and the position of FIG. 2C.

When button 150 is pressed and protruding portion 149 is pushed radially inward, second end 144 of hook 140 may press against an inner surface of body 112, such that a rotational motion is imparted to first end 142, causing it to move radially inward to the position shown in FIG. 2C. Hook 140 may have an appropriate flexibility or stiffness for accomplishing the radially inward movement of first end 142 of hook 140. Alternatively or additionally, pressing protruding portion 149 radially inward may result in radially inward translation of hook 140, causing all portions of hook 140, including first end 142, to move radially inward.

First end 142 may be approximately level with a surface of body 112 or may be radially inward of a surface of body 112. First end 142 may not radially intersect protrusion 130 in the third configuration of FIG. 2C. Therefore, hook 140 may not inhibit movement of lever 120 in the first direction. Alternatively, first end 142 may be shaped such that first end 142 and protrusion 130 radially intersect one another, but protrusion 130 is able to glide over first end 142 when it is radially depressed as in FIG. 2C. For example, barb 147 may have a ramp-like shape to allow for such gliding.

While depressing button 150, a user may move unlocked lever 120 in the first direction. After second end 134 of protrusion 130 is further in the first direction than first end 142 is (e.g., clear of first end 142), the user may release button 150 and continue to move lever 130 in the first direction.

In use, an operator may position a distal end of a duodenoscope in a desired location. A tool may be passed through a sheath of the duodenoscope until it protrudes from the distal end of the duodenoscope. Locking mechanism 100 may be in the configuration of FIG. 2A. The user may then move lever 120 in the second direction in order to raise an elevator of the duodenoscope. The user may move lever 120 until locking mechanism automatically transitions to the configuration of FIG. 2B. The user may not be required to depress button 150 in order to transition the locking mechanism to the second configuration. Instead, the geometries and properties of hook 140 and protrusion 130 may facilitate automatic locking once protrusion 130 passes first end 142 of hook 140. Hook 140 may flex radially inward as protrusion 130 passes first end 142 of hook 140. Hook 140 may engage protrusion 130 in order to lock lever 120 when the elevator is in a raised position. The operator may be free to remove a finger or thumb from lever 120 while lever 120 is locked. When the user desires to lower the elevator, the user may depress button 150 in order to move first end 142 of hook 140 radially inward, allowing protrusion 130 to pass radially outward of first end 142 of hook 140 as lever 120 is moved in the first direction.

Parameters of locking mechanism 100 may be varied in order to calibrate amount of forces required to lock and/or unlock lever 120. For example, sizes and shapes of first end 142 of hook 140 (including barb 147) and protrusion 130 may be varied in order to adjust interactions between those components and an amount of force required to transition lever 120 into a locked position and an amount of locking force provided. Aspects of protruding portion 149 and/or button 150 may also be varied in order to adjust an amount of unlocking force required to unlock lever 120.

Figure 3A:
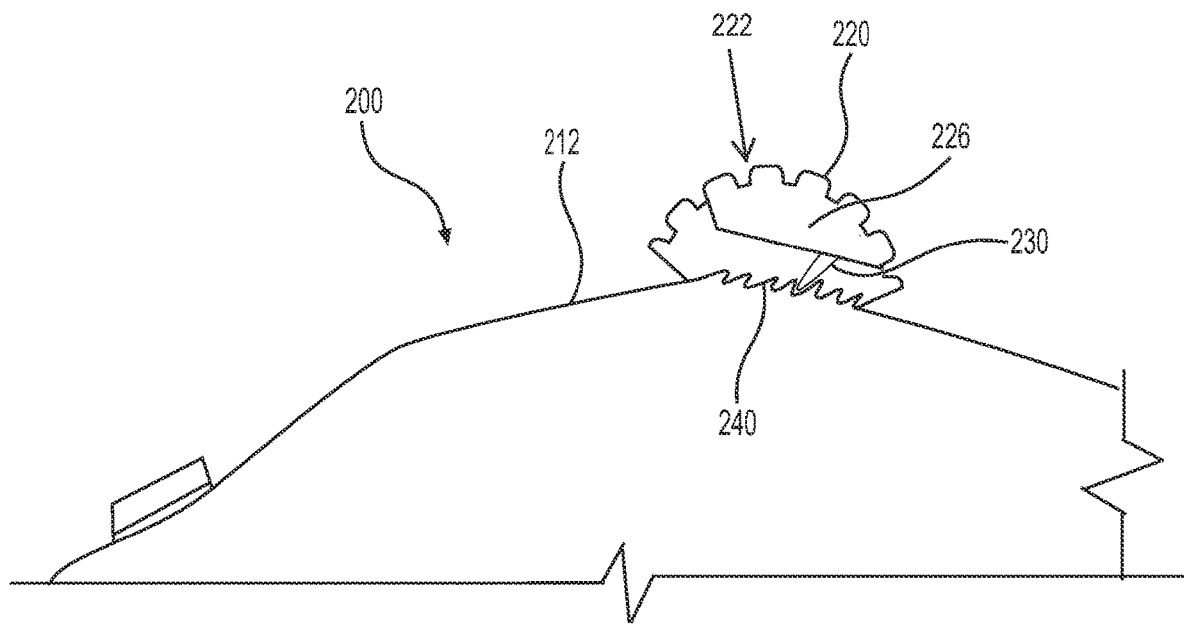
Figure 3B:
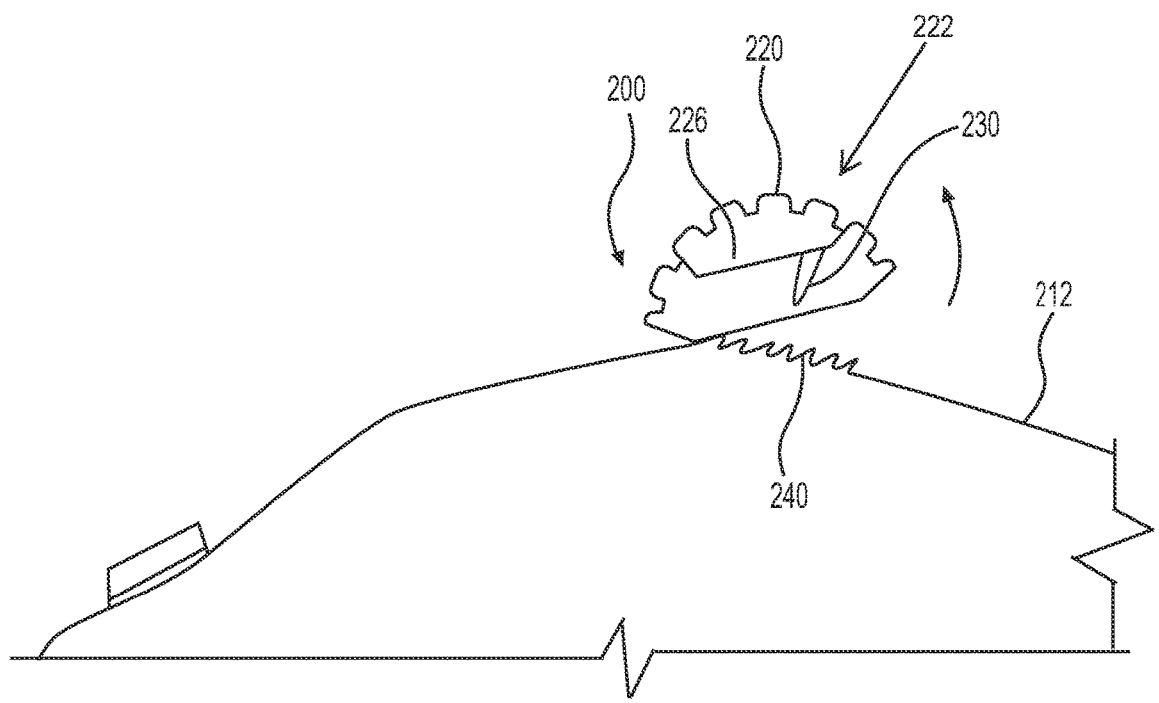

FIGS. 3A and 3B show an alternative locking mechanism 200. Locking mechanism 200 may make use of a ratcheting mechanism. Locking mechanism 200 may include an actuator, such as a lever 220, which may include a contact portion 226. Lever 220 and contact portion 226 may have any of the qualities of levers 20, 120 and contact portions 26, 226, respectively. A protrusion 230 may extend radially inward from a radially inward surface of contact portion 226, toward a surface of body 212. Body 212 may have any of the features of bodies 12, 112. Protrusion 230 may be have features similar to a pawl and may flex relative to a surface of contact portion 226.

Body 212 may have teeth 240 formed on a surface thereof in, for example, a sawtooth pattern. Teeth 240 may form engaging portions. Teeth 240 may be angled in the second direction (toward the right in FIGS. 3A-3B), which may be a direction that lever 220 is moved to raise an elevator controlled by lever 220. Teeth 240 may be integrally formed with body 212, of the same material as body 212, or may be formed of a separate piece or separate pieces secured to body 212. Teeth 240 may extend along all or a portion of body 212 along which lever 220 is movable and may protrude from body 212. For example, teeth 240 may be disposed along a range for which locking of lever 220 is desired.

Protrusion 230 and teeth 240 may have complementary shapes so that, when lever 220 is moved in at least the second direction (toward the right in FIGS. 3A and 3B), protrusion 230 can flex radially inward as a radially inward tip of protrusion 230 engages with and moves over teeth 240. Engagement of protrusion 230 with teeth 240 may provide tactile or auditory feedback to a user that lever 220 (and the elevator controlled thereby) are within a certain movement range. For example, engagement of protrusion 230 with teeth 240 may indicate to a user that the elevator is raised to a particular angle.

Lever 220 may have a pivotable portion 222. Pivotable portion 222 may be pivotable to a remainder of lever 220 (e.g., an arm of lever 220). A hinge may be disposed between pivotable portion 222 and a remainder of lever 220. Pivotable portion 222 may be biased into the configuration of FIG. 3A, in which a radially inner surface of contact portion 226 is approximately parallel to a surface of body 212. Biasing may occur via springs at a hinge of lever 220 or via shape memory properties of lever 220. A user may use a thumb or a finger to pivot or toggle pivotable portion 222 in the direction shown by the arrow in FIG. 3B. Pivoting of pivotable portion 222 may cause projection 230 to move radially away from a surface of body 212 and teeth 240.

In use, an operator may position a distal end of a duodenoscope in a desired location. A tool may be passed through a sheath of the duodenoscope until it protrudes from the distal end of the duodenoscope. The user may then move lever 220 in the second direction, while pivotable portion 222 is in the configuration of FIG. 3A, in order to raise an elevator of the duodenoscope. The user may move lever 220 until protrusion 230 engages teeth 240. After protrusion 230 engages teeth 240, lever 220 may be movable in the second direction (as long as another feature, such as a stop, does not prevent movement beyond a desired range). However, engagement of protrusion 230 with teeth 240 may inhibit lever 220 from moving in the first direction. Engagement between teeth 240 and protrusion 230 may cause locking of lever 220 in a particular position (e.g., a position in which the elevator is raised or at another desired position). The operator may be free to remove a finger or thumb from lever 220 while lever 220 is thusly locked. When the user desires to move the lever 220 in the first direction (e.g., to lower the elevator), the user may pivot pivotable portion 222 to the configuration shown in FIG. 3B. Pivoting of pivotable portion 222 may cause lever protrusion 230 to disengage from teeth 240, thereby unlocking lever 220 and allowing lever 220 to be moved in the first direction (e.g., to lower the elevator).

Locking mechanism 200 may include a plurality of segments with teeth 240 to provide a plurality of locking locations for lever 120 and a corresponding plurality of locked positions for the elevator controlled by lever 120. Smooth segments, without teeth 240, may punctuate the plurality of segments with teeth 240.

Figure 4A:
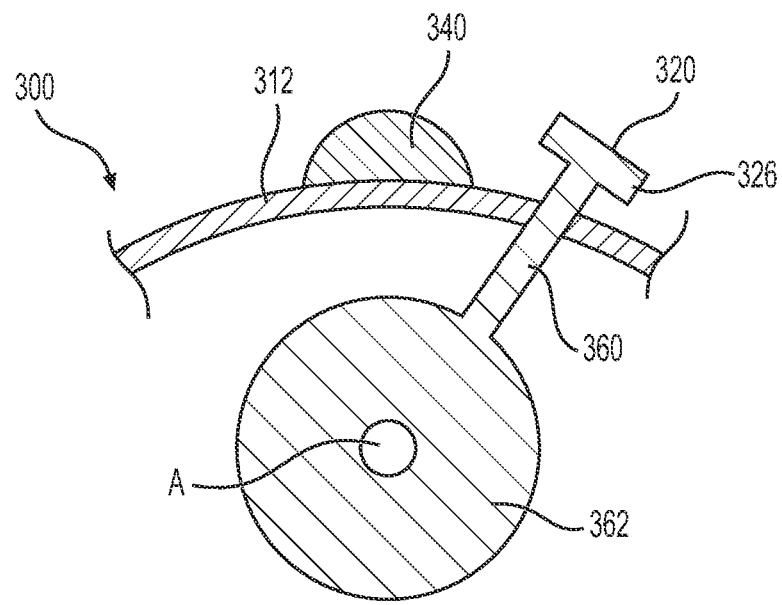
Figure 4B:
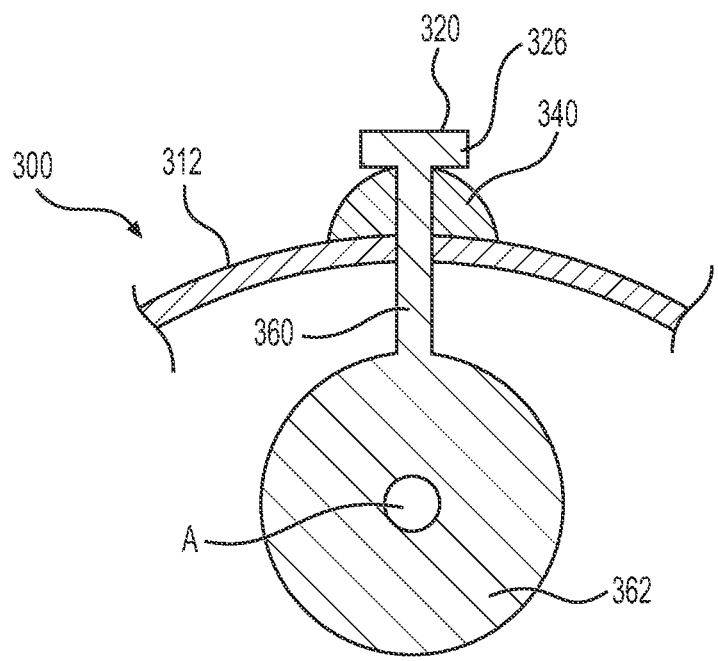

FIGS. 4A-4B show cross-sectional views of another exemplary locking mechanism 300. Locking mechanism 300 may include an actuator, such as a lever 320 which may control movement of an elevator at a distal end of a duodenoscope. Lever 320 may have any of the properties of levers 20, 120, 220, above. Lever 320 may have a contact surface 326, an arm 360, and a rotating portion 362, rotatable about an axis A. Rotating portion 362 may be washer-shaped and may be disposed exterior to or internal to body 312. Arm 360 may extend radially outward from rotating portion 362 and may terminate in contact portion 326. Arm 360 may be narrower than rotating portion 362. Contact portion 326 may protrude outward relative to a longitudinal axis of arm 360. Lever 320 may have alternative configurations, including those described above with respect to levers 20, 120, 220.

A stop 340 may be disposed on a surface of a handle body 312 and may form an engaging portion. Body 312 may have any of the properties of bodies 12, 112, 212, above. Stop 340 may protrude radially outwardly from the surface of handle body 312. Stop 340 may be shaped and sized to interact with a radially inward surface of lever 320. As shown in FIG. 4A, stop 340 may have a cross-sectional shape that is a portion of a circle or oval. Stop 340 may be disposed to one side of arm 360 or may include a channel formed therein to allow passage of arm 360 therethrough.

Lever 320 may move freely while it is not aligned with and/or engaging with stop 340. When a portion of lever 320, such as an inner surface of contact portion 326, is aligned with and/or engaging with an outer surface of stop 340, lever 320 may contact stop 340, causing a frictional force between lever 320 and stop 340.

The frictional force between lever 320 and stop 340 may depend on properties of lever 320 and/or stop 340. For example, materials used to form surfaces of lever 320 and stop 340 may affect the frictional forces therebetween. Surface treatments of lever 320 and stop 340 may also affect the frictional forces between lever 320 and stop 340. For example, roughening of lever 320 and/or stop 340 may increase frictional forces between lever 320 and stop 340. Stop 340 (or surfaces of lever 320) may be include flexible and/or compressible materials (e.g., rubber) in order to increase frictional forces between lever 320 and stop 340.

Frictional forces between lever 320 and stop 340 may be calibrated to enable the frictional forces to cause a locking effect between lever 320 and stop 340 while allowing a user to manually move lever 320 past stop 340. A desired frictional force may depend upon properties of the duodenoscope (e.g., the forces exerted on the elevator of the duodenoscope due to tension on the shaft of the duodenoscope), user properties, type of procedure, or other factors. Frictional forces between lever 320 and stop 340 may be established at manufacture or may be adjustable by a user.

Although FIGS. 3A and 3B show one stop 340, a plurality of stops 340 may be used. For example, a stop 340 may be located in positions corresponding to predetermined configurations of the elevator (fully raised, fully lowered, partially raised, etc.). Stops 340 may be located at ends of a travel path of lever 320 (as far as lever 320 can travel in either direction), or between ends of a travel path of lever 320.

In use, a user may adjust lever 320 freely when portions of lever 320 are not engaging with stop 340. When a surface of lever 320 (e.g., a surface of contact portion 326) contacts stop 340, lever 320 may be locked by frictional forces between lever 320 and stop 340. The user may be free to remove a finger or thumb from the elevator while it is so locked. The user may unlock lever 320 by exerting a sufficient force to overcome the frictional force between stop 340 and lever 320.

Figure 4C:
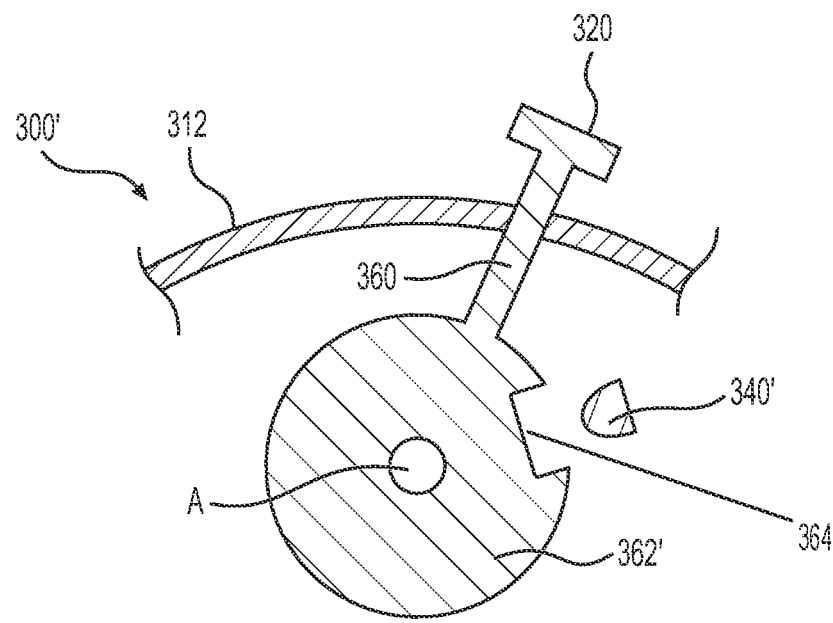
Figure 4D:
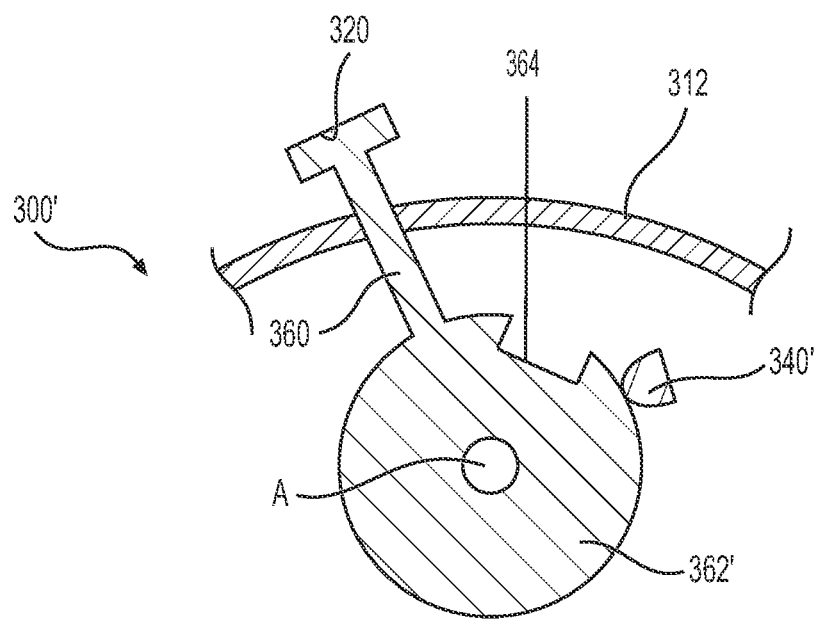

FIGS. 4C and 4D show another exemplary locking mechanism 300'. Locking mechanism 300' may function similarly to locking mechanism 300. Locking mechanism 300' may have the properties of locking mechanism 300, except as specified herein.

While locking mechanism 300 may include a stop 340 on an exterior surface of body 312, stop 340' may be disposed within an interior of body 312. Stop 340' may be secured to any suitable structure within body 312.

Rotating portion 362' may also be disposed within body 312. Rotating portion 362' may have any of the properties of rotating portion 362, except rotating portion 362' may be shaped so that a surface of rotating portion 362' sometimes engages with stop 340' and other times does not engage with stop 340'. For example, as shown in FIG. 4D, rotating portion 362' may have portions of varying radial dimension. As shown in FIG. 4D, rotating portion 362' may have a cutout portion 364 or recess causing a corresponding portion of rotating portion 362' to have a smaller radius than a remainder of rotating portion 362.' When cutout portion 364 is aligned with stop 340' (FIG. 4C), lever 320 may be freely movable. When cutout portion 364 is not aligned with stop 340', rotating portion 362' may engage with stop 340', resulting in a frictional force that serves as a brake, as described above. As shown in FIGS. 4C and 4D, cutout 364 may form a small subset of a circumference of rotating portion 362', so that a majority of rotating portion 362' is configured to engage with stop 340'. Alternatively, cutout 364 may comprise a greater proportion of a circumference of rotating portion 362'. Rotating portion 362' may include multiple cutout portions 364 that do not engage with stop 340' and multiple portions that do engage with stop 340'.

The principles regarding locking mechanism 300, described above, also apply to locking mechanism 300', including those regarding calibrating a frictional force between rotatable portion 362' and stop 340'. In use, in the first configuration of FIG. 4C, stop 340' may be aligned with cutout 364, lever 320 may be freely movable. On either direction of cutout 364 are surfaces of rotating portion 362 that may engage with stop 340'. When lever 320 is rotated so that cutout 364 no longer aligns with stop 340' (FIG. 4D), stop 340' may engage with a surface of rotatable portion 362', causing a frictional force that locks lever 320. To unlock lever 320, the user may exert a force on lever 320 to overcome the frictional force.

Figure 5A:
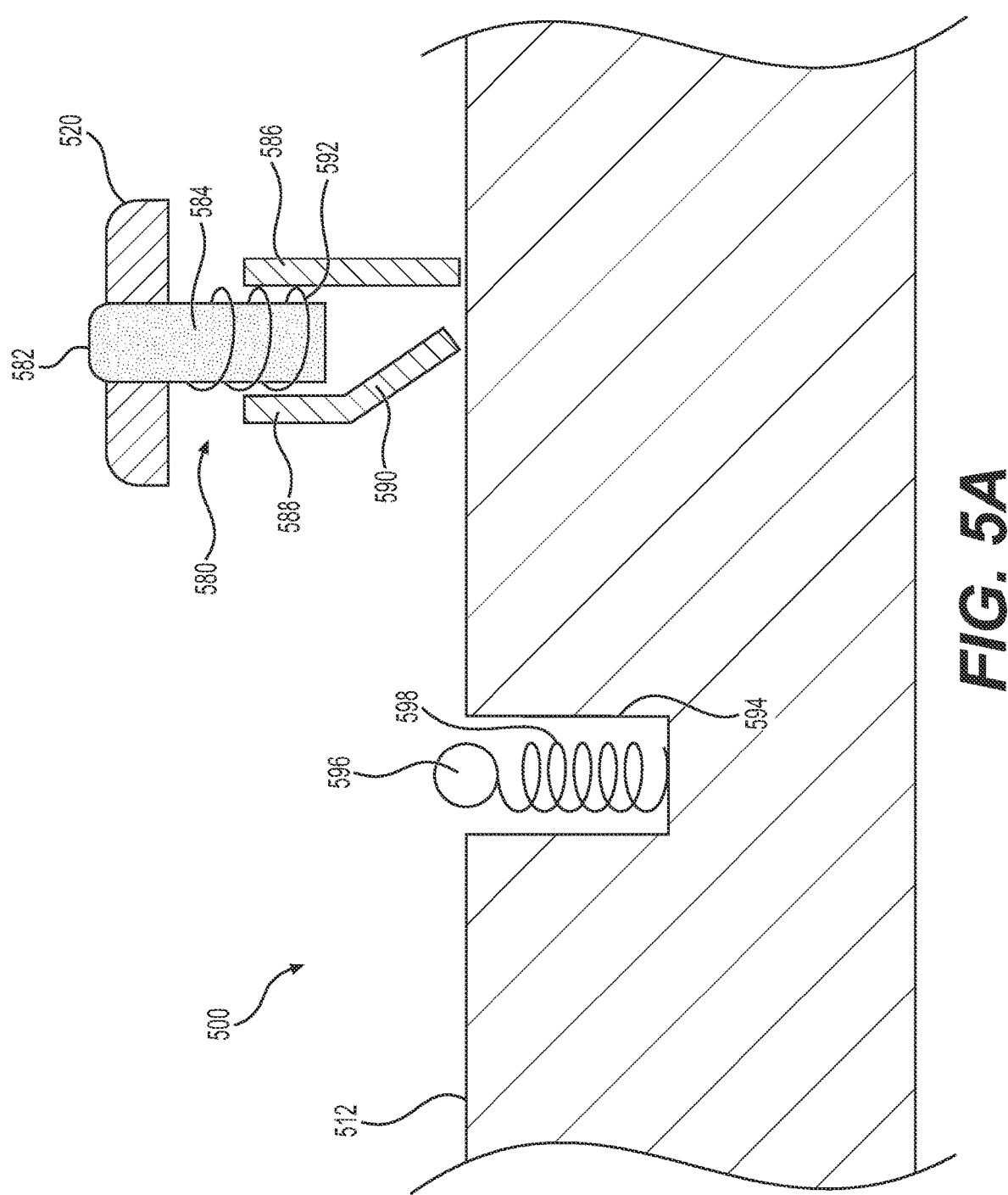

FIGS. 5A-5C show another exemplary locking mechanism 500. Locking mechanism 500 may include an actuator, such as a lever 520, which may have any of the features of levers 20, 120, 220, 320. Lever 520 may include an actuation assembly 580 that transitions lever 520 between a first configuration (FIGS. 5A and 5B) and a second configuration (FIG. 5C). Actuation assembly 580 may include a button 582. Button 582 may extend through a center or other portion of lever 520 or alongside lever 520.

In FIGS. 5A and 5B, button 582 is shown in a depressed position. FIG. 5C shows button 582 in an unbiased, neutral position in which button 582 is not depressed. A spring 592 is disposed about a shaft 584 of button 582 in order to bias button 582 into the undepressed position of FIG. 5C. Alternative mechanisms to spring 592, such as shape memory materials, may be used to bias button 582 into the configuration of FIG. 5C.

Wall portions 586 and 588 may extend at least partially around shaft 584 and spring 592. For example, wall portions 586 and 588 may be portions of a structure that completely circumferentially surrounds shaft 584 (e.g., a tube). Alternatively, wall portions 586 and 588 may be discrete pieces that only partially surround shaft 584. Wall portions 586 and 588 may be straight or curved.

Wall portion 588 may include a movable portion 590. In the activated configurations of FIGS. 5A and 5B, when button 582 is depressed/activated, movable portion 590 may form a ramped edge. Movable portion 590 may form a radially inward (toward a surface of a body 512, which may have any of the properties of bodies 12, 112, 212, 312) portion of wall portion 588. In the activated configuration (FIGS. 5A and 5B), movable portion 590 may be angled toward wall portion 586 relative to a remainder of wall portion 588. In the configuration of FIG. 5C, in which button 582 is in its neutral, unactivated position, wall portion 588, including movable portion 590, may be approximately straight, and movable portion 590 may be approximately parallel or coaxial with a remaining, non-movable portion of wall portion 588. In the straight configuration of wall portion 588, movable portion 590, and an entirety of wall portion 588 may be approximately parallel to wall portion 586. Straight wall portion 588 and wall portion 586 may be approximately perpendicular to a surface of body 512. In the configuration of FIG. 5C, wall portion 588 and wall portion 586 may have radially inward ends that are proximate to or touching a surface of body 512. Button 582 may be operationally coupled to movable portion 590 in order to activate movable portion 590 to cause wall portion 588 to transition from the approximately straight configuration of FIG. 5C to the angled configuration of FIGS. 5A and 5B.

A surface of body 512 may include a cavity 594. Cavity 594 may have any suitable shape. For example, cavity 594 may have square sides or a round cross-section. Cavity 594 may be disposed in a position corresponding to a location of lever 520 when the elevator is in a raised position. A body 596 may be movably disposed within cavity 594 and may be connected to a spring 598 or other biasing mechanism. Body 596 may form an engaging portion. Body 596 may include, for example, a ball bearing. Body 596 may be biased into the configuration of FIGS. 5A and 5C, wherein at least a portion of body 596 extends radially outward of a surface of body 512.

When lever 520 is not aligned with cavity 594 (as shown in FIG. 5A), lever 520 may be freely movable to raise or lower the elevator. When a user moves lever 520 to actuate an elevator, the user may depress button 582, causing movable portion 590 to adopt the angled configuration of FIGS. 5A and 5B. When movable portion 590 is in the angled configuration, as shown in FIG. 5B, a radially inward edge of movable portion 590 may move over body 596 and may exert a radially inward force on body 596 to push body 596 within cavity 594. The elevator may be in a raised position when lever 520 is in the configuration of FIG. 5B.

When the elevator is raised (or in another, lockable position corresponding to a position of lever 520 in the configuration of FIGS. 5B and 5C), the user may release lever 520 and button 582. After button 582 is released, movable portion 590 may transition to the configuration shown in FIG. 5C, in which movable portion 590 is approximately straight relative to a remainder of wall portion 588. Movable portion 590 may swing away from wall portion 586 to transition it to the configuration of FIG. 5C. Movable portion 590 may no longer be exerting a force on body 596, so spring 598 may adopt a neutral configuration, and body 596 may move radially outward to the configuration of FIG. 5C. Body 596 may be disposed radially outward of radially inward ends of wall portions 586 and 588. In the configuration of FIG. 5C, body 596 may inhibit body 596 from moving in either a first direction (to the left in FIGS. 5A-5C) or in a second direction (to the right in FIGS. 5A-5C). Properties of body 596 and spring 598 (e.g., a mass or volume of body 596 or a stiffness of spring 598) may cause body 596 to be sufficiently resilient in the configuration of FIG. 5C to prevent lever 520 from moving. Therefore, in the configuration of FIG. 5C, lever 520 may be in the locked configuration.

To unlock lever 520, button 582 may be depressed to transition lever 520 to the configuration of FIG. 5B. Movable portion 590 may exert a radially inward force on body 594 to push body 596 within cavity 594, thereby allowing movement of lever 520 in the first or second direction.

Although FIGS. 5A-5C show a movable portion of wall portion 588 and no movable portion of wall portion 586, it will be appreciated that wall portion 586 may also include a movable portion that may be transitioned between a configuration in which it is angled toward wall portion 588 and a configuration in which the movable portion is approximately straight relative to a remainder of wall portion 586. Such an additional movable portion may facilitate the use of a plurality of locking positions via a plurality of cavities 594 having bodies 596 disposed therein.

Figure 6A:
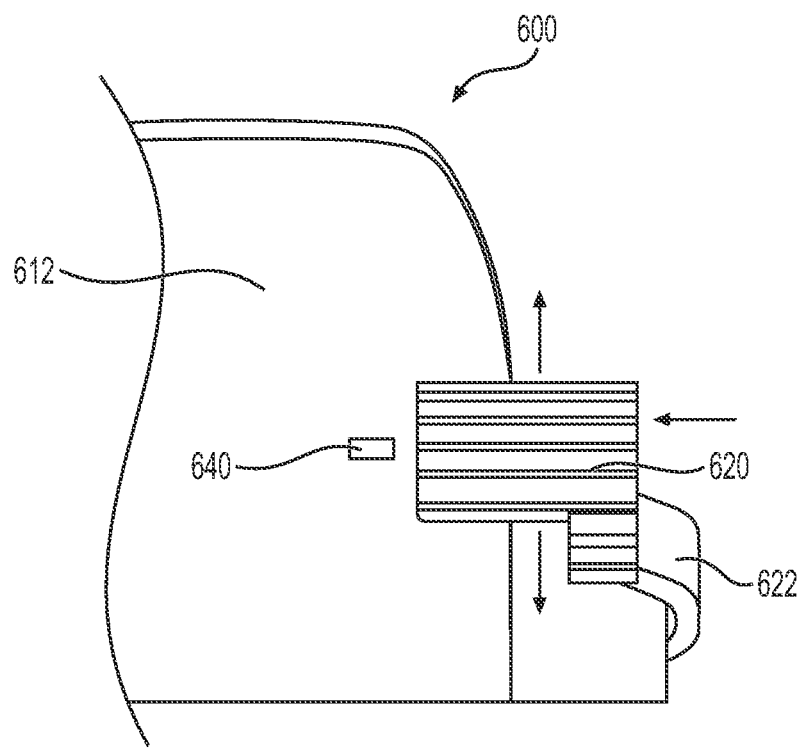
Figure 6B:
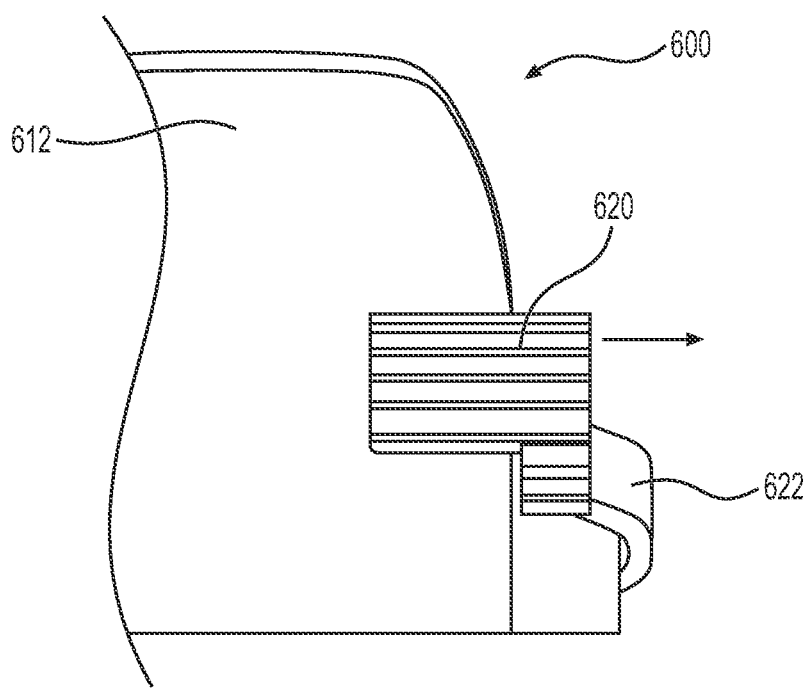

FIGS. 6A and 6B show another exemplary locking mechanism 600.

Locking mechanism 600 may have an actuator, such as a lever 620 (having any of the features of levers 20, 120, 220, 320, 520) and a body 612 (having any of the features of bodies 12, 112, 212, 312, 512). Lever 520 may be movable around a pivot point in first and second directions (up and down in FIGS. 6A and 6B) in order to raise or lower an elevator.

Body 612 may include a feature 640 formed on a surface thereof. For example, feature 640 may include a protrusion, a channel, a notch, and/or other structures. Lever 620 may have a complementary structure (not shown) on a radially inward surface thereof. For example, lever 620 may include a protrusion configured to engage with a channel of feature 640 or a recess configured to engage with a protrusion of feature 640. Although FIG. 6A shows one feature 640, it will be appreciated that a plurality of features may be disposed on a surface of body 612.

In the configuration of FIG. 6A, lever 620 may be movable in first or second directions to actuate the elevator.

Lever 620 may also be movable in a third direction (to the left in FIGS. 6A and 6B), approximately perpendicular to the first direction and the second direction. When lever 620 is aligned with feature 640, and lever 620 is moved in the third direction to the configuration shown in FIG. 6B, lever 620 may engage with feature 640 in order to retain lever 620 in the position along the first/second direction where feature 640 is disposed. Feature 640 may thus serve to lock lever 620, inhibiting rotation of lever 620 and movement of the elevator controlled thereby. In order to unlock lever 620, lever 620 may be moved in a fourth direction (to the right).

Features 640 may be at positions on surface 612 where locking of the elevator is desired. For example, features 640 may be disposed at locations along the first/second directions corresponding to a position of lever 620 where the elevator is in a raised, lowered, or partially raised configuration.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device comprising:
    a sheath configured to be inserted into a body lumen of a patient, wherein a distal end of the sheath includes an elevator for changing an orientation of a device; and
    a handle having a handle body, wherein the handle includes:
        an actuator, wherein the actuator includes a protrusion extending radially inward toward a surface of the handle body, wherein the actuator is operably connected to the elevator, wherein activation of the actuator causes movement of the elevator, and wherein the actuator is configured to be contacted by a user; and
        an engaging portion which, in at least one configuration of the handle, protrudes from the surface of the handle body toward the actuator, wherein, a first portion of the engaging portion is configured to engage with the protrusion of the actuator in a first configuration of the handle, wherein a second portion of the engaging portion is configured to be pressed radially inward by the user in order to transition the handle from the first configuration of the handle to a second configuration of the handle, wherein the first portion of the engaging portion protrudes radially outward from the handle body in at least the first configuration of the handle, and wherein the second portion of the engaging portion protrudes radially outward from the handle body in at least the first configuration of the handle;
    wherein a force exerted by the user on at least one of the actuator or the engaging portion causes the handle to transition between (a) the first configuration in which the engaging portion interacts with the actuator to inhibit movement of the actuator relative to the engaging portion and (b) the second configuration in which the actuator is movable relative to the engaging portion.

2. The medical device of claim 1, wherein the actuator includes a lever.

3. The medical device of claim 1, wherein the protrusion has a wedge shape.

4. The medical device of claim 1, wherein the engaging portion includes a hook, wherein, in the first configuration, the protrusion engages with the hook, and wherein the hook is movable to cause the handle to transition from the first configuration to the second configuration.

5. The medical device of claim 1, wherein the engaging portion includes a shape memory material.

6. The medical device of claim 4, wherein the handle further includes a button configured to exert a force on the second portion of the engaging portion.

7. The medical device of claim 1, wherein the handle is configured to be transitioned from the second configuration to the first configuration by moving the protrusion from a first side of the first portion of the engaging portion to a second side of the first portion of the engaging portion, wherein the second side is opposite the first side.

8. The medical device of claim 1, wherein the engaging portion exerts a frictional force on the actuator to inhibit movement of the actuator in the first configuration.

9. The medical device of claim 1, wherein the actuator is movable in a first direction and a second direction in order to cause movement of the elevator.

10. A method comprising:
    contacting an actuator and exerting a force on the actuator in order to move the actuator from a first position to a second position, thereby (a) raising an elevator of a distal tip of a duodenoscope from a lowered configuration to a raised configuration and (b) causing the actuator to encounter an engaging portion on a surface of a handle body of the duodenoscope, wherein a first portion of the engaging portion is configured to engage with the actuator in the first position, wherein a second portion of the engaging portion is configured to be pressed radially inward by a user in order to transition the actuator from the first position to the second position, wherein the first portion of the engaging portion protrudes radially outward from the handle body in at least the first position, and wherein the second portion of the engaging portion protrudes radially outward from the handle body in at least the second position;
    ceasing contact with the actuator, wherein, after contact with the actuator is ceased, the elevator is retained in the raised configuration;
    exerting a force on the actuator or the engaging portion; and
    moving the elevator from the second position to the first position, thereby lowering the elevator from the raised configuration to the lowered configuration.

11. The method of claim 10, wherein the engaging portion includes a shape memory material.

* * * * *